US005756712A

United States Patent [19]

Sabesan

[11] Patent Number: 5,756,712
[45] Date of Patent: May 26, 1998

[54] PEPTIDODISACCHARIDES AS OLIGOSACCHARIDE MIMETICS

[75] Inventor: Subramaniam Sabesan, Wilmington, Del.

[73] Assignee: E. I. du Pont de Nemours and Company, Wilmington, Del.

[21] Appl. No.: 787,838

[22] Filed: Jan. 23, 1997

[51] Int. Cl.$^6$ .............................. C07H 3/04; C08B 37/00
[52] U.S. Cl. ..................... 536/53; 536/17.2; 536/124; 514/25; 514/53; 514/54
[58] Field of Search ................. 536/17.2, 53, 124; 514/25, 53, 54

[56] References Cited

U.S. PATENT DOCUMENTS 5,312,903   5/1994   Linna et al. ......................... 530/351

FOREIGN PATENT DOCUMENTS

Wo 96/27379   9/1996   WIPO.

OTHER PUBLICATIONS

Fuchs et al. *Chemische Berichte* 1975, 108(7), 2254–60.
Fuchs et al. *Carbohydrate Research* Jul. 1976, 49, 267–273.
Fuchs et al. *Carbohydrate Research* 1975, 45(1), 135–141.
Muller, C. et al. "Novel Oligosaccharide Mimetics by Solid-phase Syntheses", *J. Chem. Soc., Chem. Commun.*, pp. 2425–2426 (1995).
McDevitt, Jason P. and Lansbury, Peter T. Jr. "Glycosamino Acids: New Building Blocks for combinatorial Synthesis", *J. Am. Chem. Soc.* 118, pp. 3518–3828 (1996).
Nicolaou, K.C. et al. "Carbonucleotoids and Carbopeptoids: New Carbohydrate Oligomers", *Tetrahedron Letters* 36(11) 1775–1778 (1995).
Graf von Roedern, E. et al., "Synthesis and Conformational Analysis of Linear and Cyclic Peptides Containing Sugar Amino Acids", *J. Am. Chem. Soc.*, 118, pp. 10156–10167 (1996).
Sabesan, Subramaniam et al. Synthesis and Enzymatic and NMR Studies of Novel Sialoside Probes: Unprecedented, Selective Neuraminidase Hydrolysis of and Inhibition by C–6–(Methyl)–Gal Sialosides, *J. Am. Chem. Soc.*, vol. 116, No. 5, pp. 1616–1634 (1994).
Suhara, Yoshitomo et al., "Synthesis of a New Carbohydrate Mimetics: 'Carbopeptoid' containing a C–1 Carboxylate and a C–2 Amino Group", *Tetrahedron Letters*, vol. 37 No. 10 pp. 1575–1578 (1996).

*Primary Examiner*—Kathleen K. Fonda

[57] ABSTRACT

Methods are provided to replace the ether oxygen linkage of oligosaccharides with a peptide link, —NHC(O)—, where the nitrogen atom is linked to the anomeric carbon atom of the sugar. A new family of building blocks for combinational synthesis, peptidodisaccharides, is provided containing the peptide linkage. Synthesis is more facile than with the oxygen-linked carbohydrates; the resulting compounds are expected to be more stable to enzymatic and chemical hydrolysis and to be amenable to automated synthesis.

10 Claims, No Drawings

PEPTIDODISACCHARIDES AS OLIGOSACCHARIDE MIMETICS

FIELD OF THE INVENTION

This invention concerns peptidodisaccharides wherein the bonding between the saccharide groups is via a carboxylate group on one sugar moiety and an amino group bound to the anomeric carbon atom on a second sugar moiety. Specifically disclosed are peptidodisaccharides wherein the bonding between the saccharide groups is via a C-6-carboxylate group and an amino group bound to the anomeric carbon atom. Also disclosed is a process for preparation of the compounds. These compounds are expected to be useful as enzyme inhibitors.

TECHNICAL BACKGROUND

Host cell surface oligosaccharides serve as receptor ligands for protein molecules such as enzymes, antibodies and lectins, and they initiate many critical biological reactions. Unfortunately, these receptor ligands also initiate many harmful biological reactions by providing attachment sites for viruses, toxins, bacteria, etc.

Normally in an oligosaccharide, the constituent monosaccharide groups are linked by ether oxygen linkages. This ether oxygen linkage is difficult to construct chemically. Linking methods are specific for each sugar employed. The ether oxygen linking group is susceptible to hydrolysis by glycosyl hydrolases and non-enzymatic chemical hydrolysis. This ease of hydrolysis makes it difficult to use carbohydrate structures as pharmaceuticals. Further, there are no known methods of automated syntheses for complex oxygen ether linked carbohydrates.

In the compounds of the present invention, the ether oxygen linkage is replaced by the peptide link, —NHC(O)— where the nitrogen atom of the peptide group is linked to the anomeric carbon atom of the sugar.

C. Muller et al. ("Novel Oligosaccharide Mimetics by Solid-phase Synthesis", *J Chem. Soc., Chem. Commun.,* (1995), 2425–6) disclose the synthesis of a tetramer of 2-amino-6-uronic acid. The bonding between the saccharide groups consisted of carboxylic acid amide groups formally derived from a C-6 carboxylate and a C-2 amino group.

Yoshitomo Suhara et al. ("Synthesis of a New Carbohydrate Mimetics: 'Carbopeptoid' containing a C-1 Carboxylate and a C-2 Amino Group", *Tetrahedron Letters,* (1996) Vol. 37, No. 10, pp. 1575–1578, disclose the synthesis of tetrameric D-glucosamine derivatives linked via a C-1-β-carboxylate and a C-2 α-amino group.

Jason P. McDevitt and Peter T. Lansbury, Jr. ("Glycosamino Acids: New Building Blocks for Combinatorial Synthesis", *J. Am. Chem. Soc.,* (1996) 118, 3818–3828, disclose the synthesis of 12 glycosamino acids suitable for use in the preparation of oligomeric "glycotides". None of the disclosed compounds have the nitrogen atom capable of becoming part of a peptide group linked to the anomeric carbon atom of the sugar.

K. C. Nicolaou et al. ("Carbonucleotoids and carbopeptoids: New Carbohydrate oligomers", *Tetrahedron Letters,* (1995) 36, (11), 1775–1778, depict the structure of certain carbopeptoids (peptide bond linked carbohydrates), but prepare none. The structures depicted do not have the nitrogen atom that is part of the peptide group linked to the anomeric carbon atom of the sugar.

E. Graf von Roedern et al. ("Synthesis and Conformational Analysis of Linear and Cyclic Peptides Containing Sugar Amino Acids", *J. Am. Chem. Soc.,* (1996) 118, 10156–10167, disclose the preparation of various "sugar amino acids" and their use in the synthesis of linear and cyclic peptides.

SUMMARY OF THE INVENTION

This invention concerns peptidodisaccharides wherein the bonding between the saccharide groups is via a carboxylate group on one sugar moiety and an amino group bound to the anomeric carbon atom on a second sugar moiety of the structure I:

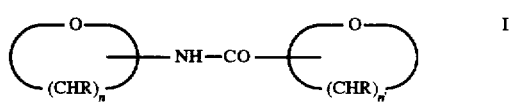

where each R, independently, is selected from the group consisting of hydrogen, hydroxy, alkoxy containing up to 8 carbon atoms, acyloxy containing up to 8 carbon atoms, acylamino containing up to 8 carbon atoms, $C_1$ to $C_{20}$ hydrocarbyl or substituted hydrocarbyl and amino; and n and n' are, independently, 4 or 5.

This invention provides peptidodisaccharides of the structure II, wherein the bonding between the saccharide groups is via a C-6-carboxylate group and an amino group bound to the anomeric carbon atom,

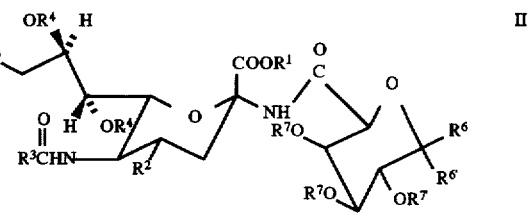

wherein $R^1$ is H, Na, or $C_1$–$C_{20}$ alkyl, $R^2$ is hydroxy, alkoxy containing from 1 to 8 carbon atoms, acyloxy containing from 1 to 8 carbon atoms, acylamino containing from 1 to 8 carbon atoms, amino, hydrogen, or guanidino;

$R^3$ is H or a $C_1$ to $C_{20}$ hydrocarbyl or substituted hydrocarbyl;

$R^4$ is H, acyl containing from 1 to 8 carbon atoms or alkyl containing 1 to 20 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$.

Also provided are peptidodisaccharides of the structure III, wherein the bonding between the saccharide groups is via a C-6-carboxylate group and an amino group bound to the anomeric carbon atom,

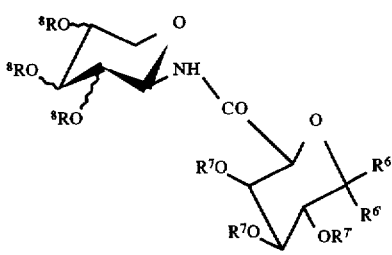

wherein $R^8$ is H, alkyl, where the alkyl contains from 1 to 20 carbon atoms, or acyl, where the acyl group contains from 1 to 8 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$.

Also provided is a process for the preparation of Compound I according to Equation I:

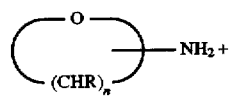

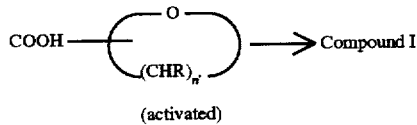

Also provided is a process for the preparation of Compounds II and III according to the Equations IIa or IIb:

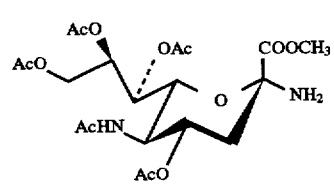

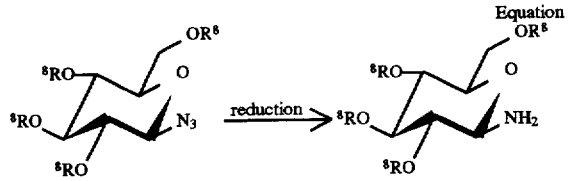

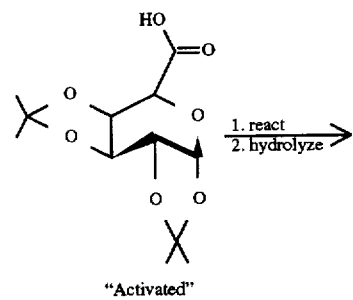

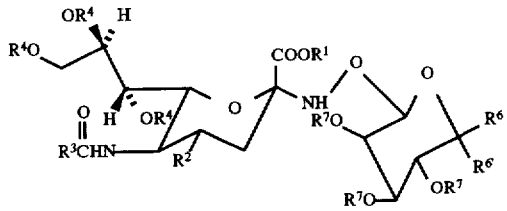

DETAILED DESCRIPTION OF THE INVENTION

The compounds of the present invention are di- or polysacharides where the link between at least two of the carbohydrate groups is the peptide group —NHC(O)— where the nitrogen atom of the peptide group is linked to the anomeric carbon atom of the sugar. The compounds can be further fuctionalized to enlarge the family.

The compounds of the present invention are expected to be synthesized by more general methods than are ether oxygen-linked carbohydrates; are expected to be more stable to enzymatic and chemical hydrolysis than is acid hydrolysis and are expected to be amenable to automated synthesis methods. A variety of mimics of natural and unnatural carbohydrates can be made by this method. The compounds may find utility as enzyme inhibitor antiviral agents and, potentially, as pharmaceuticals. Because of the wide variety of substituents that may be placed on the carbohydrate groups, the compounds are capable of extension to "libraries" of compounds by the techniques commonly used in combinatorial chemistry.

Also provided herein is a facile process for preparing the compounds of the structures I, II and III.

The route originates from azido compounds which are in turn prepared from phosphate precursors or from chloro- or bromo- compounds. U.S. Pat. No. 5,288,859 provides a useful process for the stereospecific preparation of glycosyl azides (the azido group residing at the anomeric carbon atom) by reacting a metal azide with a glycosyl phosphate triester. Experiments 3–7 are taken from U.S. Pat. No. 5,288,859. U.S. Pat. No. 5,095,123 provides a process for the glycosyl phosphate triester compounds that are useful as starting materials (glycosyl phosphates) in the preparation of glycosyl azides.

The preparative process from the azido compound precursor proceeds through the following steps:

1) The carboxylic acid group of a first monosaccharide is activated for the subsequent amidation reaction;

2) The azide group of a second monosaccharide is reduced to a primary amino group by catalytic hydrogenation, preferably over a palladium catalyst in a polar, aprotic, preferably acetonitrile solvent;

3) The amino group bearing compound and the activated carboxylic acid group are allowed to react, forming the amide linkage; and 4) The product is isolated and purified by known methods.

The products of step 2 may be isolated prior to subsequent use in step 3 or may be used in step 3 without isolation. It is preferred to use the products of steps 2 without intervening isolation. The product of step 1 is normally generated and used in situ.

There are a variety of activation methods available for use in step 1. For example, carboxylic acids are activated for subsequent reaction with amines by conversion to acid halides, by conversion to acid anhydrides, by reaction with carbonyl di imidazole, or the modified di imidazole 1,1'-Carbonylbis(3-methylimidazolium triflate) (CBMIT), by reaction with hydroxy benztriazole, by reaction with dialkyl carbodiimides or by conversion to a pentafluorophenyl ester. For sake of ease of activation and also due to the ease of byproduct separation, the preferred activation method for the carboxylic acid group is by reaction with 1,1'-Carbonylbis(3-methylimidazolium triflate) (CBMIT).

Preferred compounds of the structure I are where $R^2$ is acyloxy, most preferably acetoxy.

Compounds 2 and 4 to 8 in Table I are representative of azide starting materials used in the process of the present invention. Preparation thereof is shown in Experiments 1, and 3–7, respectively.

Experiment 2 shows the synthesis of a carboxylic acid containing monosaccharide (1,2,3,4-di-O-isopropylidene-α-D-galactopyranouronic acid, compound 3 in Table I) useful as the second component in the process of the present invention.

TABLE I

| Compound | Structure |
| --- | --- |
| Compound 1 | $R^1 = Cl, R^2 = COOCH_3$ |
| Compound 2 | $R^1 = COOCH_3, R^2 = N_3$ |
| Compound 3 | 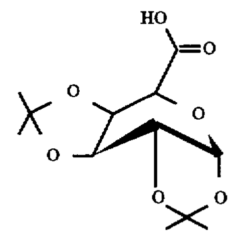 |
| Compound 4 | 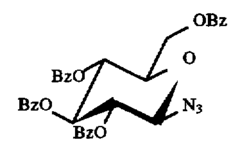 |
| Compound 5 | 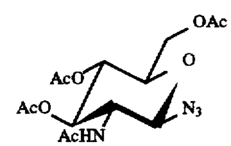 |
| Compound 6 | 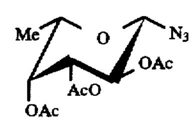 |
| Compound 7 | 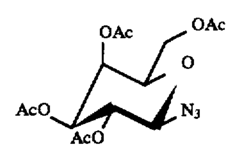 |
| Compound 8 | 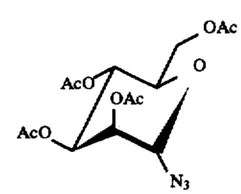 |

Experiment 8 shows the synthesis of 1,1'-Carbonylbis(3-methylimidazolium triflate) (CBMIT), a preferred coreactant in the carboxylic acid activation step 1 of the process.

Compounds 8–14 in Table II are representative of compounds of the present invention. Their synthesis is described in Examples 1–6, respectively.

TABLE II

| Compound | Structure |
|---|---|
| Compound 9 | (structure) |
| Compound 10 | (structure) |
| Compound 11 | (structure) |
| Compound 12 | (structure) |

TABLE II-continued

| Compound | Structure |
|---|---|
| Compound 13 | (structure) |
| Compound 14 | (structure) |

The processes disclosed herein are also useful for the preparation of peptide link-containing oligomers and polymers by selection of the appropriate difunctional precursors, i.e., carbohydrates containing both carboxylic acid groups and amino groups or carbohydrates containing two amino groups or two carboxylic acid groups. Branched derivatives are made possible by including trifunctional starting compounds.

Compounds of the present invention are useful as potential inhibitors of sialidase activity, and/or are expected to be resistant to neuramidase hydrolysis activity.

EXAMPLES

The following examples illustrate the process of the present invention, but are not intended to limit it in any manner. All the reagents were purchased from Aldrich Chemical Co., Milwaukee, Wis. Thin layer chromatography of the reaction mixture to monitor the progress of the reaction can be performed on precoated plates of Silica Gel 60 F.sub.254 (EM Science, Gibbstown, N.J.), and the spots were visualized with a spray containing 5% sulfuric acid in ethanol followed by heating. Column chromatography was done on silica gel 60 (230–400 mesh, EM Science). $^1$H NMR spectra were recorded at 300 MHz (GE NMR QE-300) and the $^{13}$C-NMR spectra was recorded at 75.0 and MHz with the same instrument. The hydrogen and carbon chemical shifts in deuterated chloroform, CDCl$_3$, are expressed relative to tetramethylsilane.

Isolation of the desired product is achieved by means common in the art. For example, the desired product can be isolated by high pressure liquid chromatography or column chromatography. Exemplary details are provided hereinafter in the examples.

In this specification, the meaning of abbreviations is as follows: "h" means hour(s), "min" means minute(s), "sec" means second(s), and "d" means day(s).

EXPERIMENT 1

Synthesis of methyl (5-acetamido-3,5-dideoxy-4,7, 8,9-tetra-O-acetyl-D-glycero-D-galactononulopyranoslyazide)onate (Compound 2)

To a solution of methyl (5-acetamido-3,5-dideoxy-4,7,8, 9-tetra-O-acetyl-D-glycero-D-galactononulopyranosly chloride)onate (compound 1) (2.15 g, ref. Sabesan et al., *J. Am. Chem. Soc.* (1995), 116, 1616) in acetonitrile (20 mL), sodium azide (1.7 g) was added and stirred at room temperature for 3 h. The reaction mixture was concentrated to dryness, the residue was transferred to a separatory funnel using $CH_2Cl_2$ and water, the water layer separated and the organic layer was washed with brine, dried with anhydrous $MgSO_4$ and concentrated to dryness (2.14 g). The $^1$H-NMR of the crude product confirmed the structure as that of Compound 2. $^1$H-NMR (CDCl$_3$) δ: 5.35 (H-7, H-8), 5.23 (d, NH), 5.05 (m, H-4), 4.36 (H-6), 4.07 (t, H-5), 3.90 (s, COOCH$_3$), 2.58 (dd, H-3eq), 2.15, 2.13, 2.04, 2.03, 1.88 (5×CH$_3$CO), 1.84 (dd, H-3ax).

EXPERIMENT 2

Synthesis of 1,2,3,4-di-O-isopropylidene-α-D-galactopyranouronic acid (Compound 3)

To a well stirred suspension of 1,2,3,4-di-O-isopropylidene-α-D-galactopyranose (35 g) in 1:1 CHCl$_3$—$H_2O$ (400 mL) containing sodium periodate (100 g) and benzyltriethylammonium chloride (1.5 g), RuCl$_3$ (470 mg) solution in water (5 mL) was added in drops (caution—exothermic reaction) at such rate to maintain refluxing of the reaction mixture. After 2 h, the reaction mixture was filtered over celite pad, the residue washed with $CH_2Cl_2$ and the combined filtrate was washed with water, ice cold 0.5M HCl and saturated brine solution, dried and concentrated. Weight of the crude Compound 2 was 27.0 g. $^1$H-NMR (CDCl$_3$) δ: 5.77 (d, H-1), 4.82 (dd, H-3), 4.76 (dd, H-4), 4.59 (d, H-5), 4.53 (dd, H-2).

EXPERIMENT 3

Synthesis of 2,3,4,6-tetra-O-benzoyl-β-D-glucopyranosyl azide (Compound 4)

a) Diphenyl (2,3,4,6-tetra-O-benzoyl-α-D-glucopyranosyl) phosphate

A solution of 2,3,4,6-tetra-O-benzoyl-D-glucopyranose (prepared by hydrolysis of the corresponding 1-bromide, 3.0 g, as described in Hewit, G., Fletcher, Jr., Methods in Carbohydrate Chemistry, Wolfram, M. L.; Whistler, R. L., Eds.; Vol. II, p. 226, Academic Press, New York, N.Y. (1963), in dichloromethane (40 mL) was cooled to −15° C., and 4-N,N-dimethylaminopyridine (2.4 g) and diphenyl chlorophosphate (4.2 mL) were added. The solution was stirred between −15° C. to −31 10° C. for 2 h. The reaction could not be followed by thin layer chromatography (TLC) as the α-phosphate triester product had nearly the same mobility as the starting material. Work-up of the reaction mixture, followed by chromatographic purification (ethyl acetate-hexane=3:8) gave pure (α-phosphate triester (2.5 g) along with some impure product (971 mg). The $^1$H NMR was consistent with the structure expected for the title compound.

b) 2,3,4,6-Tetra-O-benzoyl-β-D-glycopyranosyl azide

A solution of diphenyl(2,3,4,5-tetra-O-benzoyl-α-D-glucopyranosyl)phosphate (0.62 g) in anhydrous dimethylformamide (20 mL) containing sodium azide (0.5 g) was heated to 50° C. for 2 h and at 70° C. for 1 h. TLC indicated that all the starting material had disappeared and only one product was formed. The reaction mixture was evaporated to dryness and the residue was extracted with dichloromethane. This was then washed with water and then with saturated sodium bicarbonate solution. Evaporation of the solvent afforded a colorless syrup of the titled compound. As evidenced from the $^1$H NMR spectrum, the crude product was sufficiently pure and did not require chromatographic purification.

EXPERIMENT 4

Synthesis of 2-Acetamido-2-deoxy-3,4,6-tri-O-acetyl-β-D-glucopyranosyl azide (Compound 5)

a) 2-Acetamido-2-deoxy-3,4,6-tri-O-acetyl-D-glucopyranose

A solution of 2-acetamido-2-deoxy-3,4,6-tri-O-acetyl-α-D-glucopyranosyl chloride [31.0 g] in acetonitrile (125 mL) was prepared according to Horton, *Org. Synthesis*, 46, 1 (1966). (The crystalline material from which the solution was prepared was contaminated with about 5–10% of 2-acetamido-2-deoxy-1,3,4,6-tetra-O-acetyl-α-D-glucopyranose.) The solution was added to a suspension of silver carbonate (30.0 g) in 50% aqueous acetonitrile (220 mL) over a period of 15 min and the reaction was continued at room temperature for 16 h. The reaction mixture was filtered over a pad of Celite and the solution was evaporated to a volume of 150 mL. The solution was filtered again over a pad of Celite and the residue was washed with water (50 mL). The filtrate was extracted with methylene chloride (3×75 mL, most of the desired product remained in the aqueous layer). The organic layer was repeatedly extracted with water (6×100 mL) and all the aqueous solutions were combined. Thin layer chromatography examination of the aqueous layer showed the presence of a homogeneous product, whereas the organic layer contained traces of the title compound and the peracetylated material that was present in the starting material. The aqueous layer was evaporated to dryness, the residue redissolved in dichloromethane, then dried over anhydrous magnesium sulfate and evaporated to obtain an amorphous product (24.0 g). Examination by $^1$H NMR confirmed the structure of the product to be the title compound containing greater than 90% of the α-anomer.

b) Diphenyl (2-acetamido-2-deoxy-3,4,6-tri-O-acetyl-α-D-glycopyranosyl)phosphate To a solution of 2-acetamido-2-deoxy-3,4,6-tri-O-acetyl-D-glucopyranose (Example 6a, 5.0 g) in dichloromethane (400 mL) at −30° C. containing 4-N,N-dimethylaminopyridine (15.0 g), diphenyl chloro-phosphate (20.0 mL) was added and the reaction mixture was stirred between −30° C. to −25° C. for 2 h. Examination of the reaction mixture showed a single major product (the title compound) along with traces of a minor product. The reaction mixture was then diluted with dichloromethane and the organic layer was washed with ice cold water, ice cold 0.5M hydrochloric acid and a saturated solution of sodium bicarbonate. Chromatographic purification using ethyl acetate—hexane (2:3) afforded the title compound as an amorphous material (5.2 g). The structure was confirmed by $^1$H NMR.

c) 2-Acetamido-2-deoxy-3,4,6-tri-O-acetyl-β-D-glucopyranosyl azide

A solution of diphenyl(2-acetamido-2-deoxy-3,4,6-tri-O-acetyl-6O-D-glucopyranosyl)phosphate (0.7 g) in anhydrous dimethylformamide (20 mL) containing sodium azide (0.5 g) was heated to 50° C. for 1 h. The reaction mixture was evaporated to dryness and the residue was extracted with dichloromethane. This was then washed with water and then with saturated sodium bicarbonate solution. Evaporation of the solvent afforded a colorless syrup of the titled compound. $^1$H NMR indicated the crude product (0.46 g) contained essentially the title compound only.

EXPERIMENT 5

Synthesis of 2,3,4-Tri-O-acetyl-β-D-fucopyranosyl azide (Compound 6)

a) 2,3,4-Tri-O-acetyl-L-fucopyranose

L-Fucose (46.0 g) was acetylated with acetic anhydride in pyridine and the crude acetate obtained was treated with 30% hydrogen bromide in acetic acid. The crude bromide in acetone (150 mL) was added to a vigorously stirred suspension of silver carbonate (35.0 g) in 50% aqueous acetone (340 mL) over a period of 90 min. After 30 min the solution was filtered over a pad of diatomaceous earth and the filtrate was evaporated to near dryness. The residue was then dissolved in dichloromethane and the organic layer was successively washed with water, ice-cold 0.5M hydrochloric acid and saturated sodium bicarbonate solution. After being dried over anhydrous magnesium sulfate, the solution was evaporated to a dry residue. The crude syrupy product contained about 10% of the furanose derivative in addition to the pyranose (α-anomer about 48%, β-anomer about 41%). Upon standing in the refrigerator, pure pyranose crystallized out, which was washed with ice-cold ethanol-hexane to give colorless crystals (20.5 g). $^1$H NMR showed the crystals to be greater than 90% of the α-anomer.

b) Diphenyl(2,3,4-tri-O-acetyl-α-D-fucopyranosyl)phosphate

A solution of 2,3,4-Tri-O-acetyl-L-fucopyranose (2.0 g) in dichloromethane (40 mL) containing 4-N,N-dimethylaminopyridine (1.64 g) was stirred at room temperature for 15 min. and then cooled to −10° C. Diphenylchlorophosphate (2.8 mL) was added in drops and the solution was stirred between −10° C. to 0° C. for 2 h. and at 4° C. for 1 h. The reaction mixture was then diluted with dichloromethane and the organic layer was washed with ice cold water, ice cold 0.5M hydrochloric acid and saturated solution of sodium bicarbonate. Chromatographic purification using ethyl acetate-hexane (2:3) afforded the title compound as a syrup, 2.0 g. The structure was confirmed by $^1$H NMR.

c) 2,3,4-Tri-O-acetyl-β-D-fucopyranosyl azide

A solution of diphenyl(2,3,4-tri-O-acetyl-α-D-fucopyranosyl)-phosphate (2.0 g) in anhydrous dimethylformamide (80 mL) containing sodium azide (2.0 g) was heated to 50° C. for 2 h and processed as described in the synthesis of Compound 5, part c (Experiment 4). The product was purified by chromatography on a column of silica gel using ethyl acetate—hexane (3:8) as eluant to obtain the title compound (1.13 g).

EXPERIMENT 6

Synthesis of 2,3,4,6-Tetra-O-acetyl-β-D-galactopyranosyl azide (Compound 7)

a) 2,3,4,6-Tetra-O-acetyl-D-galactopyranose was prepared as in Example 3 of U.S. Pat. No. 5,288,859.

b) Diphenyl (2,3,4,6-tetra-O-acetyl-α-D-galactopyranosyl) phosphate 2,3,4,6-Tetra-O-acetyl-D-galactopyranose (3.0 g, recrystallized from benzene) was converted to the title compound as described in the synthesis of Compound 6, part b (Experiment 5). The yield of the product was 3.9 g. $^1$H NMR (CDCl$_3$) confirmed structure.

c) 2,3,4,6-Tetra-O-acetyl-β-D-galactopyranosyl azide

A solution of diphenyl(2,3,4,6-tetra-O-acetyl-α-D-galactopyranosyl)phosphate (2.94 g) in anhydrous dimethylformamide (30 mL) containing sodium azide (2.2 g) was heated to 50° C. for 24 h. The reaction mixture was evaporated to dryness and the residue was extracted with dichloromethane. This was then washed with water and then with saturated sodium bicarbonate solution. Evaporation of the solvent afforded a colorless syrup of the titled compound. The product was purified by chromatography on a column of silica gel using ethyl acetate-hexane (3:8) as eluant to obtain the title compound (1.49 g).

EXPERIMENT 7

Synthesis of 2,3,4,6-Tetra-O-acetyl-α-D-mannopyranosyl azide (Compound 8)

a) Diphenyl (2,3,4,6-tetra-O-acetyl-β-D-mannopyranosyl) phosphate

To a solution of tetra-O-acetyl-β-D-mannopyranose (3.0 g) in dichloromethane (50 mL) at room temperature containing 4-N,N-dimethylaminopyridine (DMAP) (2.4 g), a solution of diphenylchlorophosphate (4.2 mL) in dichloromethane (20 mL) was added during 60 min. After 2 h, the reaction was worked up and the products were isolated by chromotography using 3:8 ethyl acetate-hexane as eluant. After elution of the less polar alpha phosphate (937 mg), the eluant was changed to 2:3 ethyl acetate-hexane to afford the major beta phosphate (3.85 g). The structures were confirmed by $^1$H- and $^{13}$C-NMR.

b) 2,3,4,6-Tetra-O-acetyl-α-D-mannopyranosyl azide

A solution of Diphenyl (2,3,4,6-tetra-O-acetyl-β.-D-mannopyranosylphosphate (0.62 g) in anhydrous dimethylformamide (20 mL) containing sodium azide (0.5 g) was heated to 50° C. for 2 h and at 70° C. for 1 h. TLC indicated that all the starting material disappeared and only one product was formed. The reaction mixture was evaporated to dryness and the residue was extracted with dichloromethane. This was then washed with water and then with saturated sodium bicarbonate solution. Evaporation of the solvent afforded a colorless syrup of the titled compound (86.1% yield). As evidenced from the $^1$H NMR spectrum, the crude product was sufficiently pure and did not require chromatographic purification. The structure was confirmed by $^1$H- and $^{13}$C-NMR.

EXPERIMENT 8

Preparation of 1,1'-Carbonylbis(3-methylimidazolium triflate) (CBMIT)

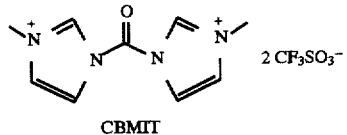

CBMIT

The CBMIT reagent for the activation of carboxyl group was prepared by a modified procedure of the reported one by Rapoport et al. (Saha et al., *J. Am. Chem. Soc.* 1989, 111, 4856).

Carbonyldiimidazole (CDI, 16.2 g) was dissolved in DCM (300 mL) and methyl triflate (32.8 g) was added in drops over a period of 2 h. The oily deposit obtained during the course of the addition was dissolved in minimum acetonitrile. It was then stirred at room temperature for 30 min and the contents of the flask was concentrated to dryness under anhydrous conditions. The dry residue was left under high vacuum. This gave a pale yellow solid (42.9 g).

EXAMPLE 1

Synthesis of Compound 9

Step-1

A solution of the glycosyl azide 2 (726 mg) in acetonitrile (60 mL) containing 10% palladium on carbon (96 mg) was stirred under hydrogen atmosphere for 45 min. Completion of the reaction was ensured by examining the reaction by TLC on silica gel, using ethylacetae-hexane-ethanol as eluant. The reaction mixture was then filtered over a pad of Celite and the filtrate was used as such in the next step.

Step-2

To a solution of the carboxylic acid 3 (410 mg) in acetonitrile (10 mL), 1,1'-Carbonylbis(3-methylimidazolium triflate) (CBMIT, 780 mg) was added and stirred for 5 min. It was then added to the filtrate from step-1 and stirred under dry nitrogen atmosphere for 16 h. Some amount of starting material still remained at this time. Additional portion of carboxylic acid (210 mg) activated with CBMIT (390 mg) in acetonitrile (5 mL) was added and the reaction was continued for another 72 h. The reaction mixture was concentrated under reduced pressure, the residue dissolved in DCM, washed with water, ice-cold 0.5M HCl, saturated sodium bicarbonate solution, dried and concentrated to dryness. The product was purified by chromatography on a column of silica gel using ethylacetate as eluant. Weight of the Compound 9 was 583 mg. $^1$H-NMR (CDCl$_3$) δ: 5.63 (d, H-1), 5.33 (dd, H-7'), 5.26 (d, NH), 5.22 (m, H-8'), 5.11 (m, H-4'), 4.65 (d , H-3), 4.58 (dd, H-4), 4.36 (dd, H-9'), 4.28 (dd, H-6'), 4.25 (d, H-5), 3.79 (s, COOCH$_3$), 2.92 (H-3'eq), 2.12, 2.08, 2.03, 1.89 (5×CH$_3$CO), 1.98 (dd, H-3'ax), 1.53, 1.45, 1.35, 1.32 (isopropylidene methyls). $^{13}$C-NMR (CDCl$_3$) δ: 170.9, 170.5, 170.3, 170.0, 168.4, 109.6, 109.4, 96.2, 83.3, 73.3, 71.7, 70.7, 70.6, 70.4, 70.3, 69.3, 68.9, 67.7, 61.7, 52.9, 49.5, 37.5, 26.0, 25.8, 24.8, 24.3, 23.19, 21.0–20.8.

EXAMPLE 2

Synthesis of Compound 10

Glycosyl azide 4 (525 mg) was hydrogenated with palladium on carbon (85 mg) under hydrogen (60 min) as described above for the synthesis of Compound 9 (Step-1). This was then coupled to the activated carboxylic acid (297 mg) with CBMIT (507 mg) as described above for the preparation of Compound 9 (Step-2) and the product was purified by chromatography on silica gel. Weight of the Compound 10 was 550 mg. $^1$H-NMR (CDCl$_3$) δ: 8.07–7.3 (benzoate groups), 5.94 (t, H-3'), 5.73 (t, H-4'), 5.72 (d, H-1'), 5.58 (d, H-1), 5.43 (t, H-2'), 4.60 (dd, H-6'a), 4.52 (d, H-3 and H-4), 4.49 (dd, H-6'b), 4.31 (H-5), 4.29–4.25 (H-5' and H-2), 1.50, 1.30, 0.89, 0.73 (isopropylidene methyls). $^{13}$C-NMR (CDCl$_3$) δ: 169.3, 166.2, 165.9, 165.6, 165.1 (5×C=O), 133.4–128.4 (benzoate carbons), 109.24, 109.17, 96.2, 77.8, 74.1, 73.5, 71.2, 71.1, 70.7, 70.2, 69.1, 68.7, 26.0, 24.9, 24.8, 23.4.

EXAMPLE 3

Synthesis of Compound 11

Glycosyl azide 5 (251 mg) was hydrogenated with palladium on carbon (40 mg) under hydrogen (15 min) as described above for the synthesis of Compound 9 (Step-1). This was then coupled to the activated carboxylic acid (240 mg) with CBMIT (442 mg) as described above for the preparation of Compound 9 (Step-2). Weight of the crude Compound 11 was 407 mg. $^1$H-NMR (CDCl$_3$) δ: 7.52 (d, NH-1'), 5.78 (d, NH-2'), 5.60 (d, H-1), 5.17 (t, H-1'), 5.14 (t, H-4'), 5.05 (t,H-3'), 4.62 (m, H-4 and H-3), 4.30 (m, H-2), 4.29 (s, H-5), 4.28 (dd, H-6'a), 4.19 (m, H-2'), 4.09 (dd, H-6'b), 3.76 (m, H-5'), 2.10, 2.04, 2.03, 1.88 (4×Ac), 1.50, 1.37, 1.32 and 1.30 (4×isopropylidene methyls). $^{13}$C-NMR (CDCl$_3$) δ: 171.5, 170.7, 170.6, 169.7, 169.2, 109.4, 109.1, 96.3, 79.2, 73.9, 73.5, 71.5, 70.7, 70.4, 68.7, 67.6, 61.7, 53.3, 26.0, 25.9, 24.8, 24.2, 23.1, 20.76, 20.66, 20.57.

EXAMPLE 4

Synthesis of Compound 12

Glycosyl azide 6 (521 mg) was hydrogenated with palladium on carbon (40 mg) under hydrogen (45 min) as described above for the synthesis of Compound 9 (Step-1). This was then coupled to the activated carboxylic acid (470 mg) with CBMIT (891 mg) as described above for the preparation of Compound 9 (Step-2 and the product was purified by chromatography on silica gel. Weight of the Compound 12 was 650 mg. $^1$H-NMR (CDCl$_3$) δ: 7.20 (d, NH), 5.59 (d, H-1), 5.27 (dd, H-4'), 5.25 (t, H-1'), 5.18 (t, H-2'), 5.12 (dd, H-3'), 4.67 (dd, H-3), 4.64 (dd, H-4), 4.36 (dd, H-2), 4.26 (d, H-5), 3.92 (m, H-5'), 2.19, 2.02, 2.00 (3×Ac), 1.50, 1.40, 1.38 (4×isopropylidene methyls), 1.18 (d, H-6'). $^{13}$C-NMR (CDCl$_3$) δ: 170.5, 170.4, 169.9, 169.4 (4×C=O), 109.7, 109.1, 96.3, 77.9, 71.4, 71.3, 71.1, 70.7, 70.5, 70.3, 68.6, 68.3, 26.1–14.2.

EXAMPLE 5

Synthesis of Compound 13

Glycosyl azide 7 (115 mg) was hydrogenated with palladium on carbon (17 mg) under hydrogen (30 min) as described above for the synthesis of Compound 9 (Step-1). This was then coupled to the activated carboxylic acid (110 mg) with CBMIT (202 mg) as described above for the preparation of Compound 9 (Step-2). Weight of the crude Compound 13 was 147 mg. $^1$H-NMR (CDCl$_3$) δ: 7.24 (d, NH), 5.58 (d, H-1), 5.42 (dd, H-4'), 5.30 (dd, H-1'), 5.16 (t, H-2'), 5.08 (dd, H-3'), 4.65 (dd, H-3), 4.62 (dd, H-4), 4.32 (dd, H-2), 4.31 (H-5), 4.14 (dd, H-6'a), 4.05 (dd, H-6'b), 4.03 (m, H-5'), 2.18, 2.08, 2.05, 2.00 (4×Ac), 1.53, 1.40, 1.32, 1.30 (4×isopropylidene methyls. $^{13}$C-NMR (CDCl$_3$) δ: 170.4, 170.13, 170.08, 169.9, 169.1, 109.4, 109.2, 96.2, 77.8, 72.4, 71.3, 71.2, 70.8, 70.3, 68.6, 67.9, 67.1, 61.2, 26.0, 25.8, 24.8, 24.1, 20.8, 20.7, 20.6, 20.5.

EXAMPLE 6

Synthesis of Compound 14

Glycosyl azide 8 (200 mg) was hydrogenated with palladium on carbon (28 mg) under hydrogen (35 min) as described above for the synthesis of Compound 9 (Step-1). This was then coupled to the activated carboxylic acid (195 mg) with CBMIT (368 mg) as described above for the preparation of Compound 9 (Step-2). Weight of the crude Compound 14 was 292 mg. The $^1$H-NMR of the product indicated that both α and β anomers were present in about 3:2 ratio, respectively. The sample was complex but the structure could be assigned on the basis of signals for NH (NH$_α$=7.11, H-5$_α$=3.92 ppm, NH$_β$=7.23 and H-5$_{β2}$=3.76 ppm).

What is claimed is:

1. A peptidodisaccharide wherein the bonding between the saccharide groups is via carboxylate group on one sugar moiety and an amino group bound to the anomeric carbon atom on a second sugar moiety of the structure I:

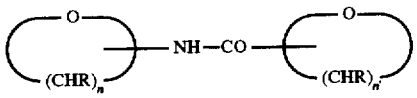

wherein each R, independently, is selected from the group consisting of hydrogen, hydroxy, alkoxy containing from 1 to 8 carbon atoms, acyloxy containing from 1 to 8 carbon atoms, acylamino containing from 1 to 8 carbon atoms, $C_1$ to $C_{20}$ hydrocarbyl o substituted hydrocarbyl and amino; and n and n' are, independently, 4 or 5.

2. A peptidodisaccharide of the structure II, wherein the bonding between the saccharide groups is via a C-6-carboxylate group and an amino group bound to the anomeric carbon atom

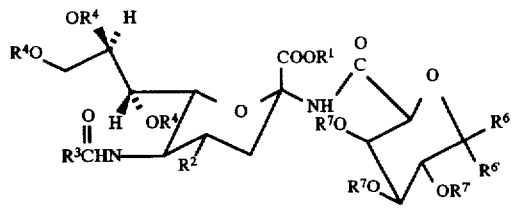

wherein $R^1$ is H, Na, or $C_1$–$C_{20}$ alkyl.

$R^2$ is hydroxy, alkoxy containing from 1 to 8 carbon atoms, acyloxy containing from 1 to 8 carbon atoms, acylamino containing from 1 to 8 carbon atoms, amino, hydrogen, or guanidino;

$R^3$ is H or a $C_1$ to $C_{20}$ hydrocarbyl or substituted hydrocarbyl;

$R^4$ is H, acyl containing from 1 to 8 carbon atoms or alkyl containing 1 to 20 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$.

3. A peptidodisaccharide of the structure III, wherein the bonding between the saccharide groups is via a C-6-carboxylate group and an amino group bound to the anomeric carbon atom,

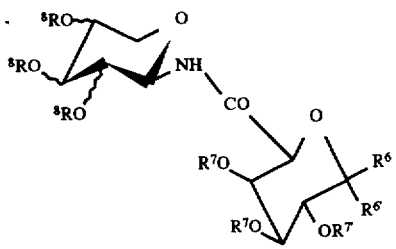

wherein $R^8$ is H, alkyl, where the alkyl contains from 1 to 20 carbon atoms, or acyl, where the acyl group contains from 1 to 8 carbon atoms;

$R^6$ and $R^{6'}$ are H, OH, a $C_1$ to $C_{20}$ alkoxy or substituted alkoxy, a mono-, di- or oligosaccharide, or an alkylideneoxy taken together with $R^{7'}$ when $R^{7'}$ is not H, provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$, $R^7$ or $R^{7'}$.

4. The peptidodisaccharide of claim 2 wherein $R_2$ is acyloxy or acetoxy.

5. A method of making a peptidodisaccharide wherein the bonding between the saccharide groups is via an amino group bound to the anomeric carbon atom and a carboxylate group of the structure I, the method comprising:

a) contacting the carboxylic acid group of a first monosaccharide group with an activating agent whereby it is activated;

b) contacting an amino group of a second monosaccharide with the activated carboxylic acid group of step a) to form an amide linkage; and c) isolating the product of step b).

6. A Method of making a peptidodisaccharide according to claim 5 wherein the bonding between the saccharide groups is via an amino group bound to the anomeric carbon atom and a C-6-carboxylate group of the structure II or via an amino group bound to the anomeric carbon atom and a C-6-carboxylate group of the structure III, the method comprising:

a) contacting the carboxylic acid group of a first monosaccharide group with an activating agent whereby it is activated;

b) contacting an amino group-bearing compound with the activated carboxylic acid group of step a) to form an amide linkage; and c) isolating the product of step b).

7. The method of claim 5 wherein the activation of the carboxylic acid group of step a) is selected from the group consisting of conversion to acid halides, conversion to acid anhydrides, reaction with carbonyl diimidazole, reaction with 1,1'-Carbonylbis(3-methylimidazolium triflate) (CBMIT), reaction with hydroxy benztriazole, reaction with dialkyl carbodiimide and by conversion to a pentafluorophenyl ester.

8. The method of claim 7 wherein the activation of the carboxylic acid group of step a) is by reaction with 1,1'-Carbonylbis(3-methylimidazolium triflate) (CBMIT).

9. The method of claim 5 further comprising reducing an azido compound to a primary amino group by catalytic hydrogenation before step b).

10. A process for making linear or branched compounds having more than two sugar wherein the bonding between the saccharide groups is via an amino group bound to the anomeric carbon atom and a carboxylate group of the structure I, the method comprising at least once a) contacting the carboxylic acid group of a first monosaccharide group with an activating agent whereby it is activated;

b) contacting an amino group-bearing compound with the activated carboxylic acid group of step a) to form an amide linkage; and c) isolating the product of step b).

* * * * *